US010272169B2

United States Patent
Lin et al.

(10) Patent No.: US 10,272,169 B2
(45) Date of Patent: Apr. 30, 2019

(54) OZONE VENTILATION SYSTEMS AND METHODS

(71) Applicant: THE BOEING COMPANY, Chicago, IL (US)

(72) Inventors: Chao-Hsin Lin, Redmond, WA (US); Sharon L. Norris, Renton, WA (US)

(73) Assignee: The Boeing Company, Chicago, IL (US)

( * ) Notice: Subject to any disclaimer, the term of this patent is extended or adjusted under 35 U.S.C. 154(b) by 256 days.

(21) Appl. No.: 15/241,438

(22) Filed: Aug. 19, 2016

(65) Prior Publication Data
US 2018/0050122 A1    Feb. 22, 2018

(51) Int. Cl.
| A61L 2/00 | (2006.01) |
| B01J 19/08 | (2006.01) |
| B01J 19/00 | (2006.01) |
| G01J 1/42 | (2006.01) |
| G01N 23/00 | (2006.01) |
| A61N 5/00 | (2006.01) |
| A61L 2/24 | (2006.01) |

(Continued)

(52) U.S. Cl.
CPC ................... *A61L 2/24* (2013.01); *A61L 2/10* (2013.01); *B64D 11/02* (2013.01); *B64D 13/06* (2013.01); *A61L 2202/14* (2013.01); *A61L 2202/25* (2013.01); *B64D 2013/0685* (2013.01)

(58) Field of Classification Search
CPC .................. A61L 2/10; A61L 2/26; A61L 2/24
USPC ....... 422/3, 23–24, 186.12, 291; 250/455.11, 250/372, 492.1
See application file for complete search history.

(56) References Cited

U.S. PATENT DOCUMENTS

| 4,819,276 | A | 4/1989 | Stevens |
| 2008/0310992 | A1* | 12/2008 | Heselton ................. A61L 2/202 422/2 |
| 2014/0115764 | A1 | 5/2014 | Cheng |

FOREIGN PATENT DOCUMENTS

| WO | WO 2014036217 | 3/2014 |
| WO | WO-2014060051 A1 * | 4/2014 ............... A61L 2/10 |

OTHER PUBLICATIONS

"Kinetics of Microbial Inactivation for Alternative Food Processing Technologies Ultraviolet Light" U.S. Food and Drug Administration,, http://www.fda.gov/Food/FoodScienceResearch/SafePracticesforFoodProcesses/ucm103137.htm.

(Continued)

*Primary Examiner* — Monzer R Chorbaji
(74) *Attorney, Agent, or Firm* — Joseph M. Butscher; The Small Patent Law Group, LLC

(57) ABSTRACT

A system and method of sanitizing one or more structures within an enclosed space includes operatively coupling an ozone ventilation control unit to an ultraviolet (UV) light assembly, an ozone sensor, and an exhaust fan, using the ozone ventilation control unit to operate the UV light assembly to emit UV light into or onto structure(s) of the enclosed space during a cleaning cycle, receiving, by the ozone ventilation control unit, an ozone presence signal indicative of an amount of ozone within the enclosed space from an ozone sensor that detects the amount of ozone within the enclosed space, using the ozone ventilation control unit to selectively activate and deactivate the exhaust fan based on the amount of ozone within the enclosed space, and using the ozone ventilation control unit to selectively activate and deactivate the UV light assembly based on the amount of ozone within the enclosed space.

15 Claims, 4 Drawing Sheets

(51) Int. Cl.
    *A61L 2/10*     (2006.01)
    *B64D 11/02*     (2006.01)
    *B64D 13/06*     (2006.01)

(56)     References Cited

OTHER PUBLICATIONS

Brian Oram, "UV Disinfection Drinking Water", http://www.water-research.net/index.php/water-treatment/water-disinfection/uv-disinfection.

Nicholas G. Reeda, "The History of Ultraviolet Germicidal Irradiation for Air Disinfection" Public Health Reports / Jan.-Feb. 2010 / vol. 125, pp. 15-27.

SangWoo Kim, et al, "In Vitro Bactericidal Effects of 625, 525, and 425nm Wavelength (Red, Green, and Blue) Light-Emitting Diode Irradiation", Photomedicine and Laser Surgery, vol. 31, No. 11, 2013, Mary Ann Liebert, Inc., pp. 554-562.

Michelle Maclean, "Inactivation of Bacterial Pathogens following Exposure to Light from a 405-Nanometer Light-Emitting Diode Array", Applied and Environmental Microbiology, Apr. 2009, vol. 75, No. 7p. 1932-1937.

\* cited by examiner

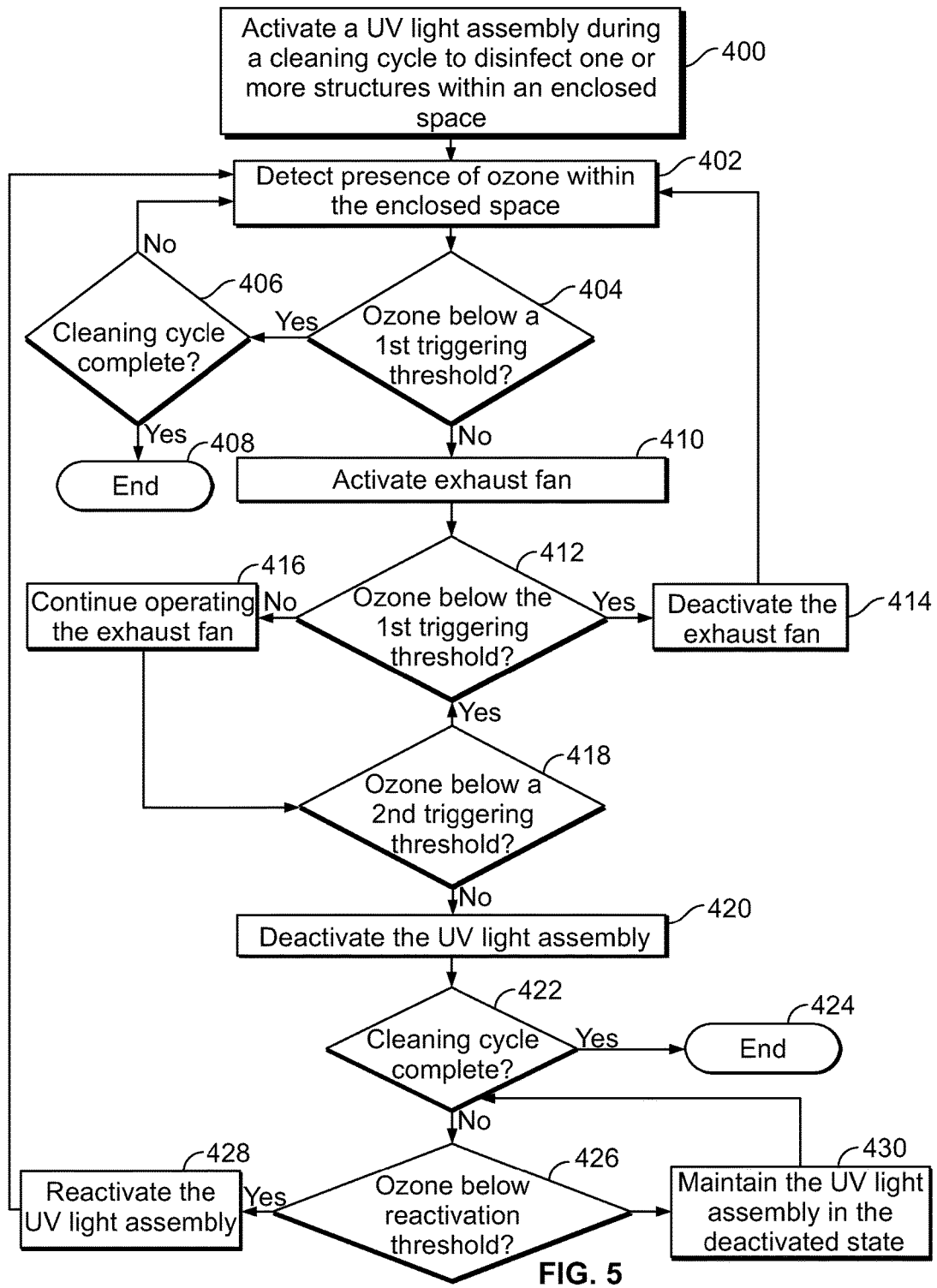

OZONE VENTILATION SYSTEMS AND METHODS

FIELD OF THE DISCLOSURE

Embodiments of the present disclosure generally relate to systems and methods for ventilating ozone within confined spaces, such as within lavatories of commercial aircraft.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. For example, it has been found that far UV light efficiently sanitizes exposed surfaces within a lavatory.

Interaction of UV light with air creates ozone. As the UV light passes through air, the interaction of the UV light with oxygen molecules generates ozone molecules.

Ozone is an irritant, both to individuals and structures. For example, certain individuals may be susceptible to breathing disorders, eye irritation, nasal irritation, and/or chest pain from prolonged exposure to ozone. Further, ozone is a reactive gas that may degrade surfaces of various structures.

Accordingly, the amount of ozone within confined spaces is typically controlled. The Federal Aviation Administration (FAA) provides regulations and guidelines regarding the presence of ozone onboard an aircraft. For example, a FAA regulatory guideline limits the amount of ozone within an internal cabin of an aircraft to an average of 100 parts ozone per billion for scheduled flight segments of more than four hours. Further, the FAA regulatory guideline also limits the amount of ozone within an internal cabin of an aircraft to 250 parts ozone per billion within a three hour peak for a flight in which ozone exceeds 180 parts ozone per billion at any time.

Accordingly, aircraft operators seek to limit the amount of ozone within an aircraft. One known disinfecting method limits the amount of generated ozone by placing a sterilizing UV light in close proximity to a surface that is to be sterilized. For example, the UV light may be within one to six inches from a surface that is to be sterilized. The close proximity of the UV light to the surface limits ozone production, as the ozone travels through a shorter distance of ambient air. However, various structures are not able to be within such a close proximity to a UV light. For example, a UV light may not be effectively positioned within a few inches of a toilet or floor within a lavatory.

SUMMARY OF THE DISCLOSURE

A need exists for a system and method of limiting the amount of ozone within a confined space. A need exists for a system and method of ventilating ozone within a confined space. A need exists for a system and method that allow for a UV light to be separated from a structure to be sanitized, such that ozone generated by the interaction of emitted UV light with ambient air is quickly, effectively, and efficiently ventilated.

With those needs in mind, certain embodiments of the present disclosure provide a system for sanitizing (for example, disinfecting or otherwise cleaning) one or more structures within an enclosed space. The system includes an ultraviolet (UV) light assembly that is configured to emit UV light into or onto the structure(s) to sanitize the structure(s). An exhaust fan is secured within the enclosed space. The exhaust fan is configured to exhaust gases from the enclosed space. An ozone ventilation system is configured to control (for example, limit, minimize, or otherwise reduce) an amount of ozone within the enclosed space. The ozone ventilation system includes an ozone sensor configured to detect the amount of ozone within the enclosed space and output an ozone presence signal indicative of the amount of ozone within the enclosed space. An ozone ventilation control unit is in communication with the UV light assembly, the exhaust fan, and the ozone sensor. The ozone ventilation control unit is configured to receive the ozone presence signal and selectively activate and deactivate the UV light and the exhaust fan based on the amount of ozone within the enclosed space.

The system may also include a monitoring station in communication with the ozone ventilation system. In at least one embodiment, the ozone ventilation control unit is configured to output an ozone status signal related to the amount of ozone within the enclosed space to the monitoring station. The monitoring station is configured to display and/or output information regarding the amount of ozone within the enclosed space.

The system may also include a door that is moveable between an open and closed position. The door in the open position allows entry into the enclosed space, while the door in the closed position closes the enclosed space. The ozone ventilation control unit may be in communication with a lock of the door. The ozone ventilation control may be configured to selectively lock and unlock the lock based on the amount of ozone within the enclosed space.

In at least one embodiment, the ozone ventilation control unit activates the exhaust fan when the amount of ozone within the enclosed space meets or exceeds a first triggering threshold. The ozone ventilation control unit may deactivate the exhaust fan when the amount of ozone within the enclosed space is below the first triggering threshold.

In at least one embodiment, the ozone ventilation control unit deactivates the UV light assembly when the amount of ozone within the enclosed space meets or exceeds a second triggering threshold that exceeds the first triggering threshold. The ozone ventilation control unit may reactivate the UV light assembly if a cleaning cycle is active and the amount of ozone within the enclosed space is below the second triggering threshold.

The ozone ventilation control unit may be configured to vary an exhaust rate of the exhaust fan based on the amount of ozone within the enclosed space.

The system may also include an ozone scrubber within the enclosed space. The ozone ventilation control unit may be in communication with the ozone scrubber. The ozone ventilation control unit may control operation of the ozone scrubber based on the amount of ozone within the enclosed space.

Certain embodiments of the present disclosure provide a method of sanitizing one or more structures within an enclosed space. The method includes operatively coupling an ozone ventilation control unit to an ultraviolet (UV) light assembly, an ozone sensor, and an exhaust fan, using the ozone ventilation control unit to operate the UV light assembly to emit UV light into or onto the structure(s) of the enclosed space during a cleaning cycle, receiving (by the ozone ventilation control unit) an ozone presence signal indicative of an amount of ozone within the enclosed space from an ozone sensor that detects the amount of ozone within the enclosed space, using the ozone ventilation control unit to selectively activate and deactivate the exhaust fan based on the amount of ozone within the enclosed space, and using the ozone ventilation control unit to selectively activate and deactivate the UV light assembly based on the amount of ozone within the enclosed space.

The method may also include coupling a monitoring station to the ozone ventilation control unit, and outputting an ozone status signal related to the amount of ozone within the enclosed space from the ozone ventilation control unit to the monitoring station to enable the monitoring station to one or both of display or output information regarding the amount of ozone within the enclosed space.

The method may also include using the ozone ventilation control unit to selectively lock and unlock a door to the enclosed space based on the amount of ozone within the enclosed space.

Certain embodiments of the present disclosure provide a vehicle that includes an internal cabin, and a lavatory within the internal cabin. The lavatory includes one or more structures that are to be sanitized, and a door that is moveable between an open and closed position. The door in the open position allows entry into the lavatory, while the door in the closed position closes the lavatory. An ultraviolet (UV) light assembly is within the lavatory. The UV light assembly is configured to emit UV light into or onto the structure(s) to sanitize the structure(s). An exhaust fan is secured within the lavatory. The exhaust fan is configured to exhaust gases from the lavatory. An ozone ventilation system is configured to control an amount of ozone within the lavatory.

BRIEF DESCRIPTION OF THE DRAWINGS

FIG. 5 illustrates a flow chart of a method of controlling ozone levels within an enclosed space during a cleaning cycle, according to an embodiment of the present disclosure.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide an ozone ventilation system that is configured to control (for example, limit, minimize, or otherwise reduce) the amount of ozone within an enclosed, confined space, such as within a lavatory, galley, or passenger cabin of an aircraft. The ozone ventilation system is operatively coupled to (for example, in communication with and able to activate and deactivate) a UV light assembly and an exhaust fan.

Figure 1:
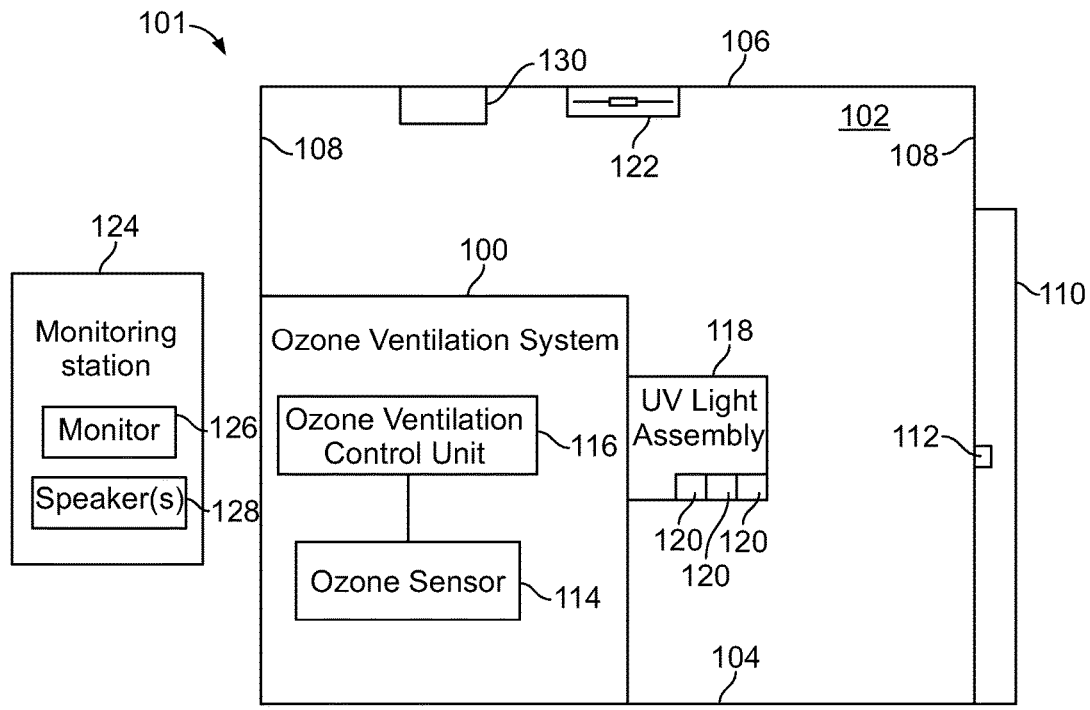
FIG. 1 illustrates a schematic diagram of an ozone ventilation system within an enclosed space, according to an embodiment of the present disclosure.

FIG. 1 illustrates a schematic diagram of an ozone ventilation system 100 within an enclosed space 102, according to an embodiment of the present disclosure. The enclosed space 102 may be defined by a floor 104, a ceiling 106, and walls 108 extending between the floor 104 and the ceiling 106. A door 110 may be moveably secured to one of the walls 108. The door 110 includes a lock 112 that is configured to securely lock the door 110 in a closed position. When the lock 112 is actuated into a locked position, the door 110 is unable to be opened. When the lock 112 is in an unlocked position, the door 110 may be opened. The enclosed space 102 may be a confined space onboard a commercial aircraft. For example, the enclosed space 102 may be a lavatory onboard an aircraft. As another example, the enclosed space 102 may be a galley onboard an aircraft. As yet another example, the enclosed space 102 may be a passenger cabin onboard an aircraft. The enclosed space 102 may or may not include the door 110. The enclosed space 102 may be within various other vehicles, structures, and/or the like. For example, the enclosed space 102 may be a room within a commercial, municipal, residential building, or a room onboard a train, bus, ship, or the like.

The ozone ventilation system 100 includes an ozone sensor 114 within the enclosed space 102. The ozone sensor 114 is coupled to (for example, in communication with through one or more wired or wireless connections) to an ozone ventilation control unit 116, which is configured to receive ozone presence signals indicative of an amount of ozone within the enclosed space 102 from the ozone sensor 114. The ozone ventilation control unit 116 may be within the enclosed space 102 (as shown in FIG. 1). Optionally, the ozone ventilation control unit 116 may be outside of the enclosed space 102. For example, the ozone ventilation control unit 116 may be part of a computer that is remotely located from the enclosed space 102. In at least one other embodiment, the ozone ventilation control unit 116 may be contained within the ozone sensor 114. While one ozone sensor 114 is shown in FIG. 1, the ozone ventilation control unit 116 may be operatively coupled to multiple ozone sensors 114 within the enclosed space 102.

The ozone ventilation system 100 is also operatively coupled to (for example, in communication with, and able to activate and deactivate) a UV light assembly 118, such as through one or more wired or wireless connections. The UV light assembly 118 includes one or more UV light elements 120 that are configured to emit UV light onto a surface and/or structure within the enclosed space 102 to sanitize (for example, disinfect or otherwise clean) the surface and/or structure. The UV light elements 120 may be light emitting diodes (LEDs), bulbs, fiber optic elements, and/or the like. In at least one embodiment, the UV light elements 120 are configured to emit far UV light. Alternatively, the UV light elements 120 may be configured to emit other types of UV light, such as UVC, UVB, or UVA light. The UV light assembly 118 may include more or less UV light elements 120 than shown. While one UV light assembly 118 is shown in FIG. 1, the ozone ventilation system 100 may be coupled to multiple UV light assemblies 118 within the enclosed space 102.

The ozone ventilation control unit 116 is also operatively coupled to (for example, in communication with and able to activate and deactivate) an exhaust fan 122, such as through one or more wired or wireless connections. The exhaust fan 122 is configured to be operated to exhaust gases (such as ozone) from the enclosed space 102 to an outside environment. In at least one embodiment, the exhaust fan 122 is a variable speed exhaust fan. In at least one embodiment, the ozone ventilation control unit 116 may be coupled to a switch that is in turn operatively coupled to the exhaust fan 122. The ozone ventilation control unit 116 may selectively close and open the switch to activate and deactivate, respectively, the exhaust fan 122.

The ozone ventilation control unit 116 may also be operatively coupled to the lock 112 of the door 110, such as through one or more wired or wireless connections. The ozone ventilation control unit 116 may be configured to lock the door 110 based on a detected level of ozone within the enclosed space. Alternatively, the ozone ventilation control unit 116 may not be operatively coupled to the lock 112.

The ozone ventilation control unit 116 may also be in communication with a monitoring station 124, such as through one or more wired or wireless connections. The monitoring station 124 may include a monitor 126 (such as a computer monitor, a television screen, a touch screen, a digital display, and/or the like), and one or more speakers 128. In at least one embodiment, the monitoring station 124 is a handheld device, such as a smart phone. The ozone ventilation control unit 116 may be configured to output ozone status signals to the monitoring station 124, such as through the one or more wired or wireless connections. The ozone status signals relate to the amount of ozone within the enclosed space 102. Information regarding the ozone status signals may be displayed on the monitor 126 (for example, graphics, text, or the like) and/or output through the speakers 128 (such as via audio signals).

The monitoring station 124 may be remotely located from the enclosed space 102. For example, the monitoring station 124 may be within an attendant area onboard an aircraft. Optionally, the monitoring station 124 may be within the enclosed space 102, or mounted to an outer wall portion of the monitoring station 124. Alternatively, the ozone ventilation system 100 may not include or otherwise be in communication with the monitoring station 124.

As shown in FIG. 1, a system 101 is provided for sanitizing (for example, disinfecting, or otherwise cleaning) one or more structures within the enclosed space 102, such as through use of the UV light assembly 118. The ozone ventilation system 100 controls (for example, limits, minimizes, or otherwise reduces) the amount of ozone within the enclosed space 102 during operation of the UV light assembly 118.

In operation, the UV light assembly 118 may be activated to sanitize one or more structures within the enclosed space 102. As the UV light element(s) 120 emit UV light, ozone molecules may be generated as the emitted UV light interacts with ambient air within the enclosed space 102.

The ozone sensor 114 detects the amount of ozone within the enclosed space 102. The ozone ventilation control unit 116 includes or is otherwise coupled to a memory that stores data regarding various triggering thresholds.

A first or fan activation triggering threshold may be an amount of ozone within the enclosed space at which the ozone ventilation control unit 116 activates the exhaust fan 122 so that ozone within the enclosed space 102 is exhausted to an outside environment. As an example, the first triggering threshold may be 50 parts of ozone per billion (ppb of ozone) within the volume of the enclosed space 102. Optionally, the first triggering threshold may be less or greater than 50 ppb of ozone within the enclosed space 102. For example, the first triggering threshold may be 10, 20, 30, or 40 ppb of ozone within the enclosed space 102. Alternatively, the first triggering threshold may be 60, 70, or 80 ppb of ozone within the enclosed space 102. As another example, the first triggering threshold may be a predetermined percentage of ozone within the volume of the enclosed space 102.

A second or UV light deactivation triggering threshold may be an amount of ozone within the enclosed space at which the ozone ventilation control unit 116 deactivates the UV light assembly 118 so that the UV light element(s) 120 no longer emit UV light, thereby preventing generation of additional ozone. As an example, the second triggering threshold may be 100 ppb of ozone within the volume of the enclosed space 102. Optionally, the second triggering threshold may be less or greater than 100 ppb of ozone within the enclosed space 102. For example, the second triggering threshold may be 60, 70, 80, or 90 ppb of ozone within the enclosed space 102. Alternatively, the second triggering threshold may be 110, 120, 130, or 140 ppb of ozone within the enclosed space 102. As another example, the second triggering threshold may be a predetermined percentage of ozone within the volume of enclosed space 102.

During a cleaning cycle, the UV light assembly 118 is active and emits UV light. In particular, the UV light element(s) 120 emit UV light into or onto a structure within the enclosed space 102 to disinfect one or more surfaces of the structure. The ozone sensor 114 detects the presence of ozone within the enclosed space 102 during the cleaning cycle. The ozone ventilation control unit 116 receives one or more ozone presence signals from the ozone sensor 114 that are indicative of the amount of the ozone within the enclosed space 102. If the ozone ventilation control unit 116 determines from the ozone presence signal that the amount of ozone within the enclosed space 102 is less than the first triggering threshold, the ozone ventilation control unit 116 takes no action with respect to the UV light assembly 118 and the exhaust fan 122.

If, however, the ozone ventilation control unit 116 determines from the ozone presence signal that the amount of ozone within the enclosed space 102 meets or exceeds the first triggering threshold, the ozone ventilation control unit 116 outputs a fan activation signal, which activates the exhaust fan 122. As the exhaust fan 122 is activated, ozone within the enclosed space 102 is dispersed within the enclosed space 102 and is exhausted to an outside environment through the exhaust fan 122.

As the exhaust fan 122 operates, the ozone ventilation control unit 116 continues to receive ozone presence signals from the ozone sensor 114. If ozone within the enclosed space 102 remains above the first triggering threshold, the ozone ventilation control unit 116 continues to operate the exhaust fan 122 to disperse and exhaust ozone from the enclosed space. If, however, the ozone ventilation control unit 116 determines that the amount of ozone within the enclosed space 102 falls below the first triggering threshold, the ozone ventilation control unit 116 may output a fan deactivation signal to the exhaust fan 122, thereby deactivating the exhaust fan 122.

In at least one embodiment, the ozone ventilation control unit 116 may deactivate the exhaust fan 122 when ozone within the enclosed space falls below a fan deactivation threshold, which may be less than the first triggering threshold. In at least one embodiment, the fan deactivation threshold is based on a detected amount of ozone within the enclosed space 102 that falls below a predetermined amount with respect to the first triggering threshold. For example, the ozone ventilation control unit 116 may deactivate the exhaust fan 122 after the detected amount of ozone within the enclosed space 102 is 50% of the first triggering threshold. Optionally, the ozone ventilation control unit 116 may deactivate the exhaust fan 122 after the detected amount of ozone within the enclosed space is greater or less than 50% of the first triggering threshold, such as 25% of the first triggering threshold, or 75% of the first triggering threshold. In at least one other embodiment, the ozone ventilation control unit 116 may deactivate the exhaust fan 122 after determining that there is no ozone within the enclosed space 102.

If, after activation of the exhaust fan 122, the ozone ventilation control unit 116 determines (through received ozone presence signals from the ozone sensor 114) that the amount of ozone within the enclosed space remains greater than the first triggering threshold, the ozone ventilation control unit 116 may output an increased fan rate signal to the exhaust fan 122, which increases the exhaust rate (for example, rotation of a fan rotor) of the exhaust fan 122. The increased exhaust rate increases the rate of ozone ventilation from the enclosed space. The ozone ventilation control unit 116 may increase the rate of the exhaust fan 122 based on additional triggering thresholds. For example, multiple increased rate triggering thresholds may be used to increase the exhaust rate of the exhaust fan 122.

If the ozone ventilation control unit 116 determines (from the ozone presence signals output by the ozone sensor 114) that ozone within the enclosed space 102 meets or exceeds the second triggering threshold (whether or not the exhaust fan is active), the ozone ventilation control unit 116 outputs a UV deactivation signal to the UV light assembly 118, thereby ceasing UV light emission therefrom.

When the ozone control unit 116 deactivates the UV light assembly 118, the ozone control unit 116 may continue to control the exhaust fan 122 to exhaust ozone from the enclosed space 102. In at least one embodiment, the ozone control unit 116 may control the exhaust fan 122 at a highest exhaust rate when ozone within the enclosed space 102 meets or exceeds the second triggering threshold. Alternatively, when the second triggering threshold is met, the ozone ventilation control unit 116 may deactivate the UV light assembly 118 and the exhaust fan 122.

After the UV light assembly 118 is deactivated based on a detected amount of ozone meeting or exceeding the second triggering threshold, the ozone ventilation control unit 116 continues to receive ozone presence signals from the ozone sensor 114. If ozone within the enclosed space 102 remains above the second triggering threshold, the ozone ventilation control unit 116 prevents the UV light assembly 118 from reactivating (and may continue to operate the exhaust fan 122 to disperse and exhaust ozone from the enclosed space 102, as described above). If, however, the ozone ventilation control unit 116 determines that the amount of ozone within the enclosed space 102 falls below the second triggering threshold, the ozone ventilation control unit 116 may output a UV reactivation signal (if a cleaning cycle is still in progress or has yet to be completed) to the UV light assembly 118, thereby reactivating the UV light assembly 118.

In at least one embodiment, the ozone ventilation control unit 116 may reactivate the UV light assembly 118 when ozone within the enclosed space falls below a UV reactivation threshold, which is less than the second triggering threshold. The UV reactivation threshold is based a detected amount of ozone within the enclosed space 102 that falls below a predetermined amount with respect to the second triggering threshold. For example, the ozone ventilation control unit 116 may reactivate the UV light assembly 118 (if a cleaning cycle is in progress, for example) after the detected amount of ozone within the enclosed space 102 is 50% of the second triggering threshold. Optionally, the ozone ventilation control unit 116 may reactivate the UV light assembly 118 after the detected amount of ozone within the enclosed space 102 is greater or less than 50% of the second triggering threshold, such as 25% of the second triggering threshold, or 75% of the second triggering threshold. In at least one other embodiment, the ozone ventilation control unit 116 may reactivate the UV light assembly 118 after determining that there is no ozone within the enclosed space 102.

As noted above, the ozone ventilation control unit 116 may be operatively coupled to the lock 112, such as through one or more wired or wireless connections. During a cleaning cycle when the UV light assembly 118 is active, the door 110 to the enclosed space 102 may be locked, so that individuals may not enter the enclosed structure 102 during the cleaning cycle. If the detected amount of ozone within the enclosed structure 102 exceeds the second triggering threshold, the ozone ventilation control unit 116 may output a lock signal to the lock 112, which ensures that the door 110 remains locked until the ozone within the enclosed structure 102 falls to a predetermined level, such as no ozone within the enclosed structure 102.

The ozone ventilation control unit 116 may also output ozone status signals to the monitoring station 124. For example, the ozone ventilation control unit 116 may output an ozone status signal to the monitoring station 124 indicating that a cleaning cycle is in progress (and that the door 110 may be locked), and/or that ozone within the enclosed structure 102 is within safe levels. As another example, the ozone ventilation control unit 116 may output an ozone status signal to the monitoring station 124 indicating that the first triggering threshold has been met (indicating presence of ozone), and that the exhaust fan 122 is active. As another example, the ozone ventilation control unit 116 may output an ozone status signal to the monitoring station 124 indicating that the second triggering threshold has been met (indicating a heightened level of ozone), and that the UV light assembly 118 has been deactivated. Information related to the ozone status signals may be displayed on the monitor 126, and/or output by the speaker(s) 128.

An ozone scrubber 130 may also be disposed within the enclosed structure 102. The ozone scrubber 130 is configured to draw ozone therein and pass the ozone through a catalyst that converts the ozone to oxygen. The ozone ventilation control unit 116 may be operatively coupled to the ozone scrubber 130, such as through one or more wired or wireless connections. The ozone control unit 116 may output a scrubber activation signal to the ozone scrubber 130 in order to activate the ozone scrubber 130 by itself, and/or in conjunction with operation of the exhaust fan 122 and/or the UV light assembly 118.

In at least one embodiment, the ozone sensor 114 and/or the ozone ventilation control unit 116 may compare ozone presence signals as output by the ozone sensor 114 with expected data for various UV light cycles. For example, based on operation of the UV light assembly 118 at a particular intensity and/or for a particular period of time, the expected amount of generated ozone within the enclosed structure 102 may be a particular expected amount. If the expected amount does not substantially match the detected amount, the ozone ventilation control unit 116 and/or the ozone sensor 114 may output a fault signal, such as to the monitoring station 124.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the ozone ventilation control unit 116 may be or include one or more processors that are configured to control operation of the exhaust fan 122, the UV light assembly 118, the ozone scrubber 130, and/or the like.

The ozone ventilation control unit 116 is configured to execute a set of instructions that are stored in one or more data storage units or elements (such as one or more memories), in order to process data. For example, the ozone ventilation control unit 116 may include or be coupled to one or more memories. The data storage units may also store data or other information as desired or needed. The data storage units may be in the form of an information source or a physical memory element within a processing machine.

The set of instructions may include various commands that instruct the ozone ventilation control unit 116 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the ozone ventilation control unit 116. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the ozone ventilation control unit 116 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
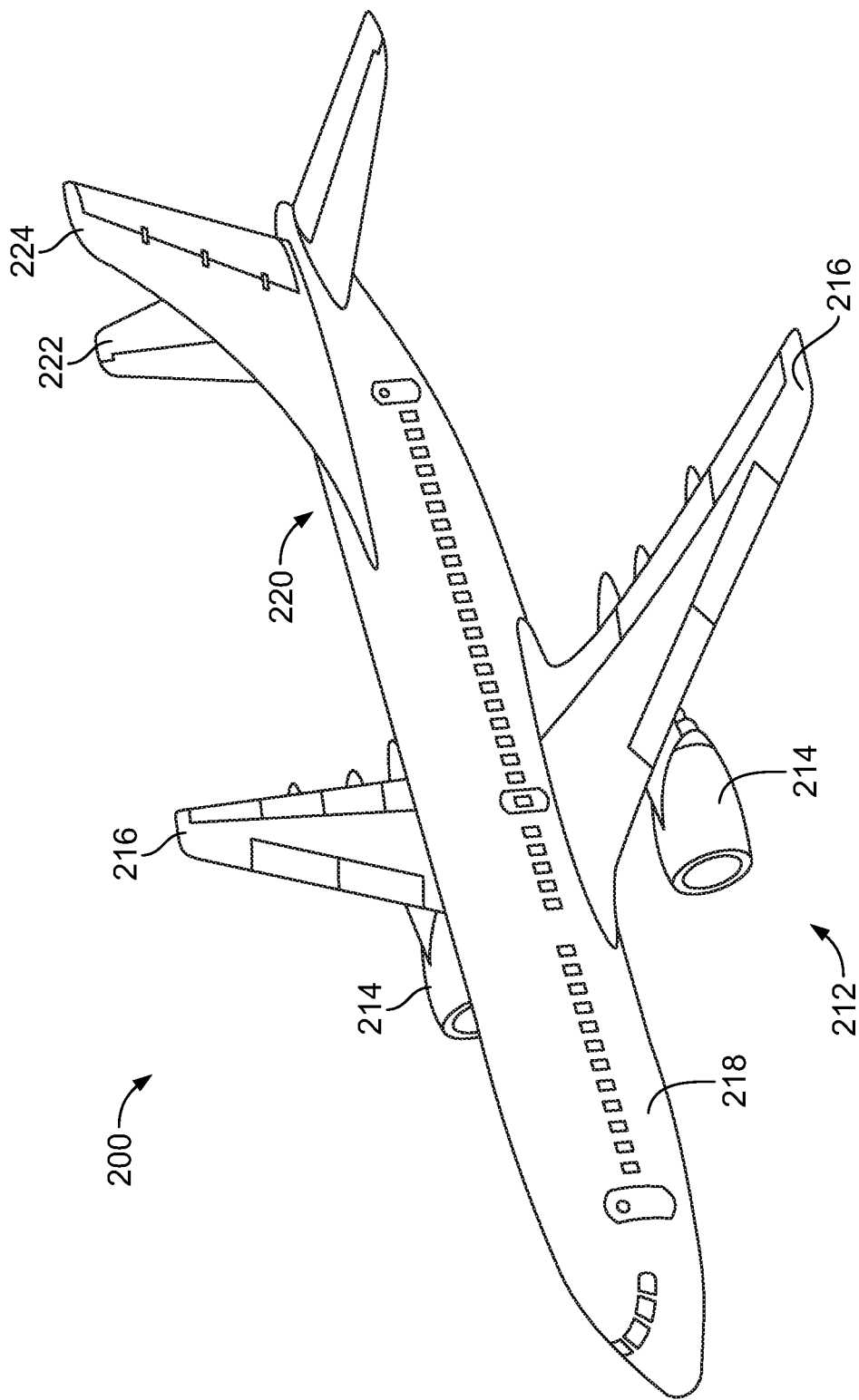
FIG. 2 illustrates a perspective top view of an aircraft, according to an embodiment of the present disclosure.

FIG. 2 illustrates a perspective top view of an aircraft 200, according to an embodiment of the present disclosure. The aircraft 200 includes a propulsion system 212 that may include two turbofan engines 214, for example. Optionally, the propulsion system 212 may include more engines 214 than shown. The engines 214 are carried by wings 216 of the aircraft 200. In other embodiments, the engines 214 may be carried by a fuselage 218 and/or an empennage 220. The empennage 220 may also support horizontal stabilizers 222 and a vertical stabilizer 224.

The fuselage 218 of the aircraft 200 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example. One or more ozone ventilation systems 100 (shown and described with respect to FIG. 1) may be located within the internal cabin.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 3A:
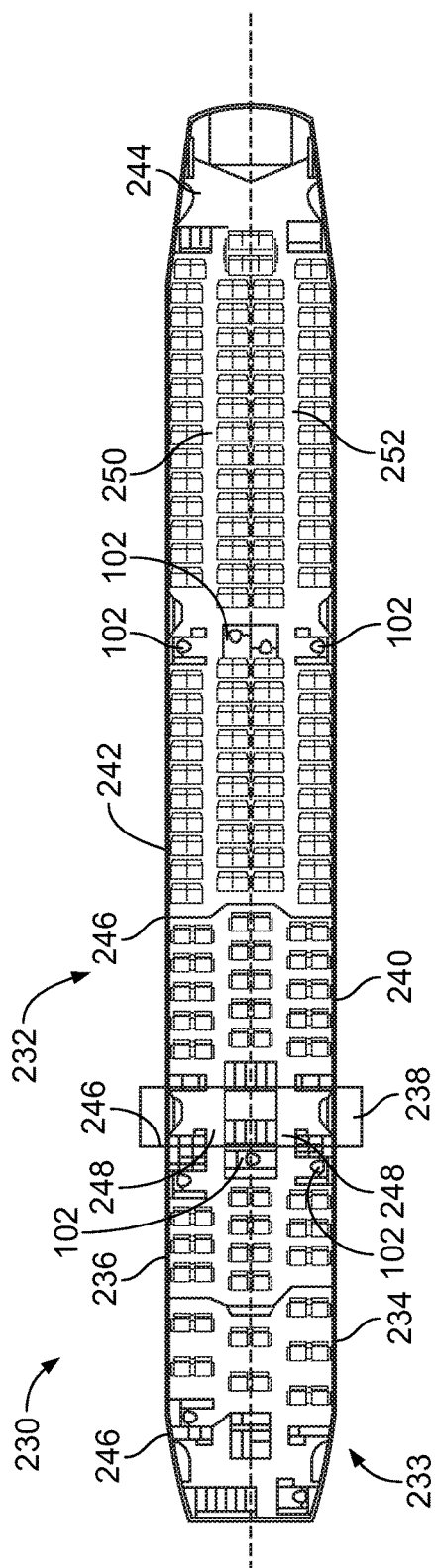
FIG. 3A illustrates a top plan view of an internal cabin of an aircraft, according to an embodiment of the present disclosure.

FIG. 3A illustrates a top plan view of an internal cabin 230 of an aircraft, according to an embodiment of the present disclosure. The internal cabin 230 may be within a fuselage 232 of the aircraft. For example, one or more fuselage walls may define the internal cabin 230. The internal cabin 230 includes multiple sections, including a front section 233, a first class section 234 (or first class suites, cabins, for example), a business class section 236, a front galley station 238, an expanded economy or coach section 240, a standard economy or coach section 242, and an aft section 244, which may include multiple chambers 104, such as lavatories and galley stations. It is to be understood that the internal cabin 230 may include more or less sections than shown. For example, the internal cabin 230 may not include a first class section, and may include more or less galley stations than shown. Each of the sections may be separated by a cabin transition area 246, which may include class divider assemblies between aisles 248.

As shown in FIG. 3A, the internal cabin 230 includes two aisles 250 and 252 that lead to the aft section 244. Optionally, the internal cabin 230 may have less or more aisles than shown. For example, the internal cabin 230 may include a single aisle that extends through the center of the internal cabin 230 that leads to the aft section 244.

One or more enclosed spaces 102, such as lavatories, may be located within the internal cabin 230. Ozone ventilation systems 100 may be used to remove ozone from the lavatories 102, such as described above with respect to FIG. 1.

Figure 3B:
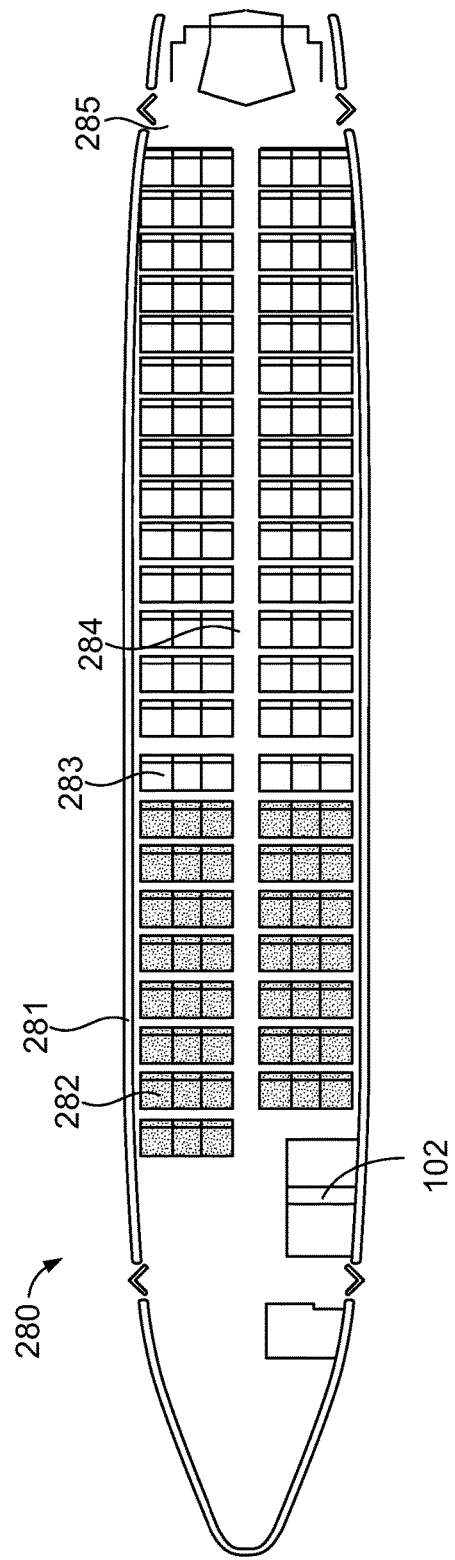
FIG. 3B illustrates a top plan view of an internal cabin of an aircraft, according to an embodiment of the present disclosure.

FIG. 3B illustrates a top plan view of an internal cabin 280 of an aircraft, according to an embodiment of the present disclosure. The internal cabin 280 may be within a fuselage 281 of the aircraft. For example, one or more fuselage walls may define the internal cabin 280. The internal cabin 280 includes multiple sections, including a main cabin 282 having passenger seats 283, and an aft section 285 behind the main cabin 282. It is to be understood that the internal cabin 280 may include more or less sections than shown.

The internal cabin 280 may include a single aisle 284 that leads to the aft section 285. The single aisle 284 may extend through the center of the internal cabin 280 that leads to the aft section 285. For example, the single aisle 284 may be coaxially aligned with a central longitudinal plane of the internal cabin 280.

One or more enclosed spaces 102, such as lavatories, may be located within the internal cabin 280. Ozone ventilation systems 100 may be used to remove ozone from the lavatories 102, such as described above with respect to FIG. 1.

Figure 4:
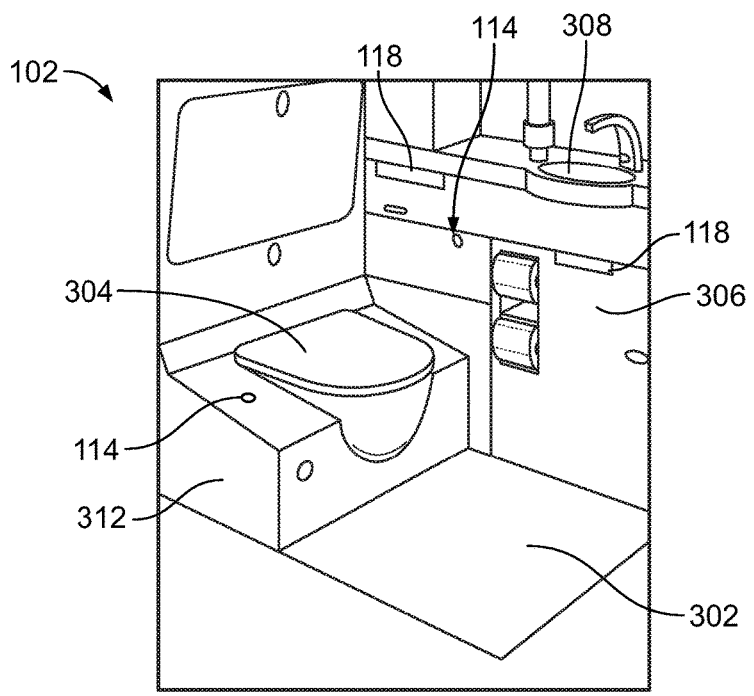
FIG. 4 illustrates a perspective internal view of a lavatory, according to an embodiment of the present disclosure.

FIG. 4 illustrates a perspective internal view of a lavatory 102, according to an embodiment of the present disclosure. As noted, the lavatory 102 is an example of the enclosed space 102 shown and described with respect to FIG. 1. The lavatory 102 may be onboard an aircraft, as described above. Optionally, the lavatory 102 may be onboard various other vehicles. In other embodiments, the lavatory 102 may be within a fixed structure, such as a commercial or residential building.

The lavatory 102 includes a base floor 302 that supports a toilet 304, cabinets 306, and a sink 308. UV light assemblies 118 are secured within the lavatory 102 and are configured to be activated during a cleaning cycle to disinfect various structures within the lavatory 102, such as the toilet 304, the floor 302, the cabinets 306, and the sink 308. The ozone sensor 114 may be mounted at a location within the lavatory 102. As shown, the ozone sensor 114 may be mounted on a housing 312 of the toilet 304. Optionally, the ozone sensor 114 may be secured to various other portions of the lavatory 102.

FIG. 5 illustrates a flow chart of a method of controlling ozone levels within an enclosed space during a cleaning cycle, according to an embodiment of the present disclosure. Referring to FIGS. 1 and 5, the method begins at 400, in which the UV light assembly 118 is activated during a cleaning cycle to disinfect one or more structures within the enclosed space 102. At 402, the ozone sensor 114 detects the presence of ozone within the enclosed space 102.

At 404, the ozone ventilation control unit 116 determines whether ozone within the enclosed space 102 is below a first triggering threshold. If the ozone detected by the ozone sensor 114 is below the first triggering threshold, the method proceeds to 406, in which the ozone ventilation control unit 116 determines whether the cleaning cycle is complete. If the cleaning cycle is complete, the process ends at 408. If, however, the cleaning cycle is not complete, the method returns to 402, in which the ozone sensor 114 continues to detect the presence of zone within the enclosed space 102.

If at 404, detected ozone within the enclosed space 102 is above the first triggering threshold, the method proceeds to 410, in which the ozone ventilation control unit 116 activates the exhaust fan 122. At 412, after the exhaust fan 122 is activated, the ozone ventilation control unit 116 then determines if the detected amount of ozone within the enclosed space 102 is below the first triggering threshold. If the detected amount of ozone is below the first triggering threshold, the method proceeds from 412 to 414, in which the ozone ventilation control unit 116 deactivates the exhaust fan 122, and the process returns to 402.

If, however, the detected amount of ozone at 412 is above the first triggering threshold, the method proceeds from 412 to 416, in which the exhaust fan 122 continues to operate to disperse and exhaust the ozone from the enclosed space 102. Then, at 418, the ozone ventilation control unit 116 determines whether the amount of ozone within the enclosed space 102 is below a second triggering threshold. If the detected amount of ozone is below the second triggering threshold at 418, the method returns to 412 from 418.

If, however, the detected amount of ozone at 418 is above the second triggering threshold, the method proceeds from 418 to 420, in which the ozone ventilation control unit 116 deactivates the UV light assembly 118. The method then proceeds to 422, in which the ozone ventilation control unit 116 determines whether the cleaning cycle is complete. If the cleaning cycle is complete at 422, the process ends at 424.

If, however, the cleaning cycle is not complete at 422, the method proceeds from 422 to 426, in which the ozone ventilation control unit 116 determines whether the amount of ozone within the enclosed space 102 is below a UV reactivation threshold. If the amount of ozone within the enclosed space is below the reactivation threshold at 426, the method proceeds to 428, in which the UV light assembly 118 is reactivated, and the method then returns to 402.

If, however, the ozone within the enclosed spaced is above the reactivation threshold at 426, the method proceeds to 430, in which the ozone ventilation control unit 116 maintains the UV light assembly 118 in the deactivated state. The process then returns to 422.

As described above, embodiments of the present disclosure provide systems and methods of limiting the amount of ozone within a confined space. Embodiments of the present disclosure provide systems and methods of ventilating ozone within a confined space. Embodiments of the present disclosure provide systems and methods that allow for a UV light to be separated from a structure to be sanitized, such that ozone generated by the interaction of emitted UV light with ambient air is quickly, effectively, and efficiently ventilated from the enclosed space.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system for sanitizing one or more structures within an enclosed space, the system comprising:
   an ultraviolet (UV) light assembly that emits emit UV light into or onto the one or more structures to sanitize the one or more structures;
   an exhaust fan secured within the enclosed space, wherein the exhaust fan exhausts gases from the enclosed space; and
   an ozone ventilation system that controls an amount of ozone within the enclosed space, the ozone ventilation system comprising:
      an ozone sensor that detects the amount of ozone within the enclosed space and outputs an ozone presence signal indicative of the amount of ozone within the enclosed space; and
      an ozone ventilation control unit in communication with the UV light assembly, the exhaust fan, and the ozone sensor, wherein the ozone ventilation control unit receives the ozone presence signal and selectively activates and deactivates the UV light and the exhaust fan based on the amount of ozone within the enclosed space,
      wherein the ozone ventilation control unit activates the exhaust fan when the amount of ozone within the enclosed space meets or exceeds a first triggering threshold,
      wherein the ozone ventilation control unit deactivates the UV light assembly when the amount of ozone within the enclosed space meets or exceeds a second triggering threshold that exceeds the first triggering threshold.

2. The system of claim 1, further comprising a monitoring station in communication with the ozone ventilation system, wherein the ozone ventilation control unit is configured to output an ozone status signal related to the amount of ozone within the enclosed space to the monitoring station, and wherein the monitoring station is configured to one or both of display or output information regarding the amount of ozone within the enclosed space.

3. The system of claim 1, further comprising a door that is moveable between an open and closed position, wherein the door in the open position allows entry into the enclosed space, wherein the door in the closed position closes the enclosed space, wherein the ozone ventilation control unit is in communication with a lock of the door, and wherein the ozone ventilation control is configured to selectively lock and unlock the lock based on the amount of ozone within the enclosed space.

4. The system of claim 1, wherein the ozone ventilation control unit deactivates the exhaust fan when the amount of ozone within the enclosed space is below the first triggering threshold.

5. The system of claim 1, wherein the ozone ventilation control unit reactivates the UV light assembly if a cleaning cycle is active and the amount of ozone within the enclosed space is below the second triggering threshold.

6. The system of claim 1, wherein the ozone ventilation control unit varies an exhaust rate of the exhaust fan based on the amount of ozone within the enclosed space.

7. The system of claim 1, further comprising an ozone scrubber within the enclosed space, wherein the ozone ventilation control unit is in communication with the ozone scrubber, and wherein the ozone ventilation control unit controls operation of the ozone scrubber based on the amount of ozone within the enclosed space.

8. A method of sanitizing one or more structures within an enclosed space, the method comprising:
   operatively coupling an ozone ventilation control unit to an ultraviolet (UV) light assembly, an ozone sensor, and an exhaust fan;
   using the ozone ventilation control unit to operate the UV light assembly to emit UV light into or onto the one or more structures of the enclosed space during a cleaning cycle;
   receiving, by the ozone ventilation control unit, an ozone presence signal indicative of an amount of ozone within the enclosed space from an ozone sensor that detects the amount of ozone within the enclosed space;
   using the ozone ventilation control unit to selectively activate and deactivate the exhaust fan based on the amount of ozone within the enclosed space, wherein the using the ozone ventilation control unit to selectively activate and deactivate the exhaust fan comprises activating the exhaust fan when the amount of ozone within the enclosed space meets or exceeds a first triggering threshold; and
   using the ozone ventilation control unit to selectively activate and deactivate the UV light assembly based on the amount of ozone within the enclosed space, wherein the using the ozone ventilation control unit to selectively activate and deactivate the UV light comprises deactivating the UV light assembly when the amount of ozone within the enclosed space meets or exceeds a second triggering threshold that exceeds the first triggering threshold.

9. The method of claim 8, further comprising:
   coupling a monitoring station to the ozone ventilation control unit; and
   outputting an ozone status signal related to the amount of ozone within the enclosed space from the ozone ventilation control unit to the monitoring station to enable the monitoring station to one or both of display or output information regarding the amount of ozone within the enclosed space.

10. The method of claim 8, further comprising using the ozone ventilation control unit to selectively lock and unlock a door to the enclosed space based on the amount of ozone within the enclosed space.

11. The method of claim 8, wherein the using the ozone ventilation control unit to selectively activate and deactivate the exhaust fan comprises deactivating the exhaust fan when the amount of ozone within the enclosed space is below the first triggering threshold.

12. The method of claim 8, wherein the using the ozone ventilation control unit to selectively activate and deactivate the UV light comprises reactivating the UV light assembly if a cleaning cycle is active and the amount of ozone within the enclosed space is below the second triggering threshold.

13. The method of claim 8, wherein the using the ozone ventilation control unit to selectively activate and deactivate the exhaust fan comprises varying an exhaust rate of the exhaust fan based on the amount of ozone within the enclosed space.

14. The method of claim 8, further comprising:
coupling the ozone ventilation control unit to an ozone scrubber within the enclosed space; and
using the ozone ventilation control unit to control operation of the ozone scrubber based on the amount of ozone within the enclosed space.

15. A vehicle comprising:
an internal cabin;
a lavatory within the internal cabin, wherein the lavatory comprises one or more structures to be sanitized, and a door that is moveable between an open and closed position, wherein the door in the open position allows entry into the lavatory, wherein the door in the closed position closes the lavatory;
an ultraviolet (UV) light assembly within the lavatory, wherein the UV light assembly emits UV light into or onto the one or more structures to sanitize the one or more structures;
an exhaust tint secured within the lavatory, wherein the exhaust fan exhausts gases from the lavatory; and
an ozone ventilation system that controls an amount of ozone within the lavatory, the ozone ventilation system comprising:
  (i) an ozone sensor that detects the amount of ozone within the lavatory and output an ozone presence signal indicative of the amount of ozone within the lavatory; and
  (ii) an ozone ventilation control unit in communication with the UV light assembly, the exhaust fan, and the ozone sensor, wherein the ozone ventilation control unit receives the ozone presence signal and selectively activates and deactivates the UV light and the exhaust fan based on the amount of ozone within the lavatory, wherein the ozone ventilation control unit is in communication with a lock of the door, and wherein the ozone ventilation control selectively locks and unlocks the lock based on the amount of ozone within the lavatory, wherein the ozone ventilation control unit activates the exhaust fan when the amount of ozone within the lavatory meets or exceeds a first triggering threshold, deactivates the exhaust fan when the amount of ozone within the lavatory is below the first triggering threshold, deactivates the UV light assembly when the amount of ozone within the lavatory meets or exceeds a second triggering threshold that exceeds the first triggering threshold, and reactivates the UV light assembly if a cleaning cycle is active and the amount of ozone within the lavatory is below the second triggering threshold; and
a monitoring station in communication with the ozone ventilation system, wherein the monitoring station receives an ozone status signal related to the amount of ozone within the lavatory from the ozone ventilation control unit, and wherein the monitoring station one or both of displays or outputs information regarding the amount of ozone within the lavatory.

\* \* \* \* \*